US012588881B2

(12) United States Patent
Birkhold et al.

(10) Patent No.: US 12,588,881 B2
(45) Date of Patent: Mar. 31, 2026

(54) PROVIDING A RESULT DATA SET

(71) Applicant: Siemens Healthcare GmbH, Erlangen (DE)

(72) Inventors: Annette Birkhold, Stuttgart (DE); Christopher Rohkohl, Brixen Im Thale (AT); Markus Kowarschik, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 614 days.

(21) Appl. No.: 17/988,138

(22) Filed: Nov. 16, 2022

(65) Prior Publication Data

US 2023/0172571 A1 Jun. 8, 2023

(30) Foreign Application Priority Data

Dec. 8, 2021 (DE) ..................... 10 2021 213 995.7

(51) Int. Cl.
*A61B 6/00* (2024.01)
*G06T 7/00* (2017.01)
*G16H 30/40* (2018.01)

(52) U.S. Cl.
CPC ............. *A61B 6/481* (2013.01); *G16H 30/40* (2018.01); *G06T 7/0012* (2013.01)

(58) Field of Classification Search
CPC .... A61B 2018/00744; A61B 2090/374; A61B 6/504; A61B 6/481; A61B 2090/3762;
(Continued)

(56) References Cited

U.S. PATENT DOCUMENTS 5,150,292 A * 9/1992 Hoffmann .............. A61B 6/507
600/431
9,082,211 B2 7/2015 Prevrhal et al.
(Continued)

FOREIGN PATENT DOCUMENTS

CN 112584768 A 3/2021
DE 102010062030 A1 5/2012
(Continued)

OTHER PUBLICATIONS

Tang, Jie, et al. "New consistency theorem of motion contaminated projection data and applications in motion artifacts correction." Medical Imaging 2012: Physics of Medical Imaging. vol. 8313. SPIE, 2012. (Year: 2012).*
(Continued)

*Primary Examiner* — Courtney Joan Nelson
(74) *Attorney, Agent, or Firm* — Lempia Summerfield Katz LLC

(57) ABSTRACT

A method for providing a result data set includes: acquiring a medical image data set of an object under examination that maps a change in the object under examination on a time-resolved basis, wherein the change starts and/or ends at different locations and at least partially different points in time within the object under examination. The method further includes identifying a spatiotemporal subregion in the image data set that maps the change in a region of interest of the object under examination, wherein the subregion is delimited spatially by the mapping of the region of interest and temporally by the earliest start and/or the latest end of the change mapped at the locations within the region of interest. The method further includes providing a result data set based on the subregion of the image data set, wherein the result data set maps the region of interest on a time-resolved basis.

17 Claims, 5 Drawing Sheets

(58) Field of Classification Search

CPC ......... G06T 2207/30104; G06T 11/003; G06T 2211/404; G06T 7/0012; G06T 2207/20224; G06T 7/254; G06T 7/38; G06V 10/25; G06V 10/751; G16H 30/40

See application file for complete search history.

(56) References Cited

U.S. PATENT DOCUMENTS

| | | | |
|---|---|---|---|
| 9,786,069 B2 | 10/2017 | Schafer et al. | |
| 10,517,556 B2 | 12/2019 | Chen et al. | |
| 2009/0016587 A1* | 1/2009 | Strobel | G06T 7/20 |
| | | | 382/130 |
| 2012/0136243 A1 | 5/2012 | Boese | |
| 2016/0015348 A1* | 1/2016 | Ohishi | A61B 6/481 |
| | | | 600/431 |
| 2017/0256077 A1* | 9/2017 | Schafer | G06T 11/008 |
| 2018/0032653 A1 | 2/2018 | Aben et al. | |
| 2018/0199905 A1 | 7/2018 | Kowarschik et al. | |
| 2018/0218521 A1* | 8/2018 | Kowarschik | G06T 11/008 |
| 2019/0347793 A1 | 11/2019 | Breininger et al. | |
| 2020/0193590 A1* | 6/2020 | Schafer | G06T 7/0016 |

FOREIGN PATENT DOCUMENTS

| | | |
|---|---|---|
| DE | 102011082440 A1 | 8/2012 |
| JP | 2008000499 A | 1/2008 |
| WO | 2016135330 A1 | 9/2016 |

OTHER PUBLICATIONS

Almekhlafi, Mohammed A., et al. "Not all "successful" angiographic reperfusion patients are an equal validation of a modified TICI scoring system." Interventional Neuroradiology 20.1 (2014): 21-27.
Liebeskind, David S., et al. "eTICI reperfusion: defining success in endovascular stroke therapy." Journal of heurointerventional surgery 11.5 (2019): 433-438.
Zaidat, Osama O., et al. "Recommendations on angiographic revascularization grading standards for acute ischemic stroke: a consensus statement." Stroke 44.9 (2013): 2650-2663.

* cited by examiner

21  Signal
24  Signal
25  Signal
26  Signal
31  Object under examination
33  X-ray source
34  Detector
37  C-arm X-ray device
38  Arm
39  Movement unit
41  Display unit
42  Input unit
PRVS  Provision unit

PROVIDING A RESULT DATA SET

The present patent document claims the benefit of German Patent Application No. 10 2021 213 995.7, filed Dec. 8, 2021, which is hereby incorporated by reference in its entirety.

TECHNICAL FIELD

The present disclosure relates to a method for providing a result data set, a provision unit, a medical imaging device, and a computer program product.

BACKGROUND

To detect changes in a region of interest (ROI) of an object under examination, (e.g., a male or female human and/or animal patient), time-resolved imaging methods may be used. The change to be detected may include a movement of a contrast agent and/or a movement of a medical object in the object under examination, in particular, the region of interest. Furthermore, the change may start and end at different locations inside the object under examination at different points in time, in particular may occur at least partially simultaneously. Because of the complexity of anatomical objects, in particular a vasculature, of the object under examination, it may be difficult for a medical operative to (e.g., visually) detect the change in the region of interest, (e.g., a spatial section of the object under examination).

To improve the mapping of the change in the object under examination, it may be possible to employ a difference imaging method, in particular, an X-ray-based difference imaging method such as digital subtraction angiography (DSA). In DSA, a mask image is frequently subtracted from one or more filling images and a difference image is provided, wherein the mask image maps the object under examination without the contrast agent and/or medical object arranged therein and the at least one filling image maps the object under examination with the contrast agent and/or medical object arranged therein. To map the dynamic over time of the change in the object under examination, multiple filling images are frequently acquired as a sequence in time and are combined with the mask image to form a time-resolved difference image. As a result, regions of the object under examination which do not change in space and/or over time and which are mapped in the mask image and the at least one filling image may be removed from the difference image. However, a disadvantage of this is furthermore often that the entire spatiotemporal mapping region of the mask image and of the at least one filling image is mapped in the difference image, as a result of which the detection, in particular the visual detection, of the change in the region of interest of the object under examination is made more difficult.

SUMMARY AND DESCRIPTION

The object of the disclosure is to improve the way in which a change in a region of interest of an object under examination is mapped.

The scope of the present disclosure is defined solely by the appended claims and is not affected to any degree by the statements within this summary. The present embodiments may obviate one or more of the drawbacks or limitations in the related art.

A first aspect of the disclosure relates to a method, (e.g., a computer-implemented method), for providing a result data set. In this case, a medical image data set of an object under examination is acquired. The image data set maps a change in the object under examination on a time-resolved basis. Furthermore, the change starts and/or ends at different locations inside the object under examination at at least partially different points in time. Furthermore, a spatiotemporal subregion is identified in the image data set, the subregion mapping the change in a region of interest of the object under examination. In this case, the subregion is delimited spatially by the mapping of the region of interest and temporally by the earliest start and/or the latest end of the change mapped at the locations within the region of interest. Moreover, the result data set is provided on the basis of the subregion of the image data set. In this case the result data set maps the region of interest on a time-resolved basis.

In this case, the acts described above of the proposed method for providing a result data set are executed consecutively and/or at least partially simultaneously. Furthermore, the acts of the proposed method may be at least partially, in particular fully, computer-implemented.

The image data set may advantageously be acquired by a medical imaging device. The medical imaging device for the acquisition of the image data set may be embodied as a magnetic resonance tomography system (MRT) and/or a computed tomography system (CT) and/or a medical X-ray device and/or a positron emission tomography system (PET) and/or an ultrasound device.

The image data set may map the object under examination spatially on a two-dimensionally (2D) and/or three-dimensionally (3D) resolved basis. Moreover, the image data set of the object under examination may map in an initial time period on a time-resolved basis. In this case, the initial time period may include multiple acquisition time points. The image data set may advantageously have multiple picture elements, in particular pixels and/or voxels. In this case, the picture elements of the image data set may each have a time intensity curve that maps the change in the object under examination as a change in intensity over time. The object under examination may be a male or female human and/or animal patient. Moreover, the change in the object under examination may be both a spatial and also a temporal change in respect of an initial, in particular preprocedural, state of the object under examination. The change in the object under examination may include a movement of a contrast agent and/or of a medical object.

As a result, the change may start and/or end at different locations inside the object under examination, in particular different spatial positions within the object under examination, at different points in time (e.g., at least partially or fully different points in time), in particular within the initial time period. In this case, the start of the change may be identified using a deviation of a current state of the object under examination compared to the initial state. Furthermore, the end of the change may be identified when the object under examination returns to its initial state. In this case, a point in time of the start and/or end of the change may be identified in each case at the different locations inside the object under examination, in particular the different spatial positions. Furthermore, the image data set may be acquired in accordance with DSA and may have a difference image of the object under examination. If the image data set maps the object under examination three-dimensionally on a spatially and temporally resolved basis, the image data set may be acquired in accordance with four-dimensional DSA (4D DSA).

The region of interest of the object under examination may include a spatial region of the object under examination that has an anatomical object such as an organ, (e.g., a hollow organ and/or a brain and/or a liver and/or a heart and/or a lung), and/or a tumor and/or a vascular malformation and/or a thrombus, and/or a predefined section of the anatomical object and/or a predefined section of a medical object arranged in the object under examination. The region of interest may advantageously include at least one vessel section, for example an artery and/or vein.

The identification of the spatiotemporal subregion in the image data set may include an identification of the picture elements of the image data set, the picture elements mapping the region of interest. In this case, the subregion may be delimited spatially, in particular two-dimensionally and/or three-dimensionally, by the mapping of the region of interest, in particular, in the image data set. The spatiotemporal subregion in the image data set may advantageously be identified as an at least partially, in particular fully, coherent set of picture elements of the image data set that maps the region of interest. Moreover, the subregion may be delimited in time by the earliest start and/or the latest end of the change mapped at the locations, in particular the spatial positions, within the region of interest. The earliest start and/or the latest end of the change mapped at the locations within the region of interest may be determined by comparing the points in time of the start and/or end of the change at the different locations within the region of interest. In particular, the subregion may map the region of interest in a further time period on a time-resolved basis, wherein the further time period is situated within the initial time period. Moreover, the further time period may correspond partially or fully to the initial time period.

The provision of the result data set may include storage on a computer-readable storage medium and/or a display of a graphical representation of the result data set on a display unit and/or a transmission to a provision unit.

The result data set may correspond to the identified spatiotemporal subregion of the image data set. Alternatively, the result data set may be generated, in particular reconstructed, on the basis of the subregion of the image data set. In this case, the result data set may map the region of interest of the object under examination two-dimensionally and/or three-dimensionally on a spatially-resolved basis. Moreover, the result data set may map the region of interest on a time-resolved basis, in particular within the further time period. In this case, the result data set may, in particular analogously to the image data set, have multiple picture elements, in particular pixels and/or voxels, which in each case have a time intensity curve. In this case, the change in the region of interest may be mapped as a temporal change in intensity in the time intensity curve of the picture elements of the result data set.

By identifying the spatiotemporal subregion in the image data set and providing the result data set on the basis of the subregion a spatiotemporal selection, in particular a spatiotemporal zoom-in to the mapping of the change in the region of interest of the object under examination, may advantageously be enabled. As a result, a particularly precise and selective mapping of the change in the region of interest of the object under examination may be enabled. As a result, the medical operative may advantageously be supported when planning a treatment strategy and/or a treatment plan, in particular an endovascular treatment plan.

In a further embodiment, the change may include a movement of a contrast agent and/or of a medical object at least in the region of interest.

The region of interest may advantageously have a hollow organ, in particular a vessel and/or a vessel section, (e.g., an artery and/or vein), wherein the contrast agent is arranged in the hollow organ. The change may include a movement of a contrast agent, in particular a contrast-enhancing and/or intensity-enhancing contrast agent, (e.g., a propagation movement and/or flow movement of the contrast agent such as a contrast agent flow and/or a movement of a contrast agent bolus), in the region of interest. In this case, the start of the change, in particular a wash-in of the contrast agent at a location within the region of interest, may be identified by a specified intensity threshold value being exceeded. Analogously, the end of the change may be identified by the specified intensity threshold value being undershot. In particular, the earliest start of the change may be determined by a minimum bolus arrival time and the latest end of the change by a maximum bolus arrival time of the contrast agent, in particular of the contrast agent bolus, in the region of interest of the object under examination.

Alternatively, or additionally, the change may include a movement of a medical object at least in the region of interest. The medical object may be embodied as an endoscope, (e.g., a laparoscope), and/or a catheter and/or a guide wire and/or an implant. The medical object, (e.g., a distal section of the medical object), may advantageously be arranged at least partially in the object under examination, in particular in the hollow organ. The movement of the medical object may include a translation and/or rotation of the medical object, in particular of the distal section, at least in the region of interest. The start of the change, in particular the start of a change in positioning of the medical object, may be identified in respect of the accuracy of positioning by a specified threshold value being exceeded. In this case, the change in positioning of the medical object, in particular of the distal section, may include a change in a spatial position and/or alignment and/or pose of the medical object. Furthermore, the end of the change, in particular the end of the change in positioning of the medical object, may be identified in respect of the accuracy of positioning by the threshold value being undershot, in particular for a specified minimum period.

The proposed form of embodiment may advantageously enable a selective spatiotemporal mapping of the movement of the contrast agent and/or of the medical object in the region of interest of the object under examination.

In a further embodiment, the subregion of the image data set mapping the region of interest may be identified manually, semi-automatically, or fully automatically.

In accordance with a first variant of the proposed form of embodiment the subregion of the image data set that maps the region of interest may be identified manually. For this, a medical operative may be shown a graphical representation of the image data set by a display unit, for example, as a scene and/or video sequence and/or difference image. The medical operative may then specify the spatiotemporal subregion of the image data set using the graphical representation of the image data set by making an input by an input unit. For this, the medical operative may specify a bounding box and/or a contour in the graphical representation of the image data set, inside which the region of interest is mapped. Moreover, the medical operative may by the input specify the further time period within the initial time period, for example, using a graphical representation of a time axis and/or of a timeline.

In accordance with a second variant of the proposed form of embodiment, the subregion of the image data set that maps the region of interest may be identified semi-automatically. For this, the medical operative may be shown a graphical representation of the image data set by the display unit. The medical operative may then, by making an input by an input unit, specify one or more spatial points and/or regions and/or points in time and/or periods in the graphical representation of the image data set that may be contained in the spatiotemporal subregion set to be identified of the image data set.

When specifying one or more spatial points and/or regions in the graphical representation of the image data set the spatial subregion in the image data set may advantageously be automatically identified, in particular completed. The automatic identification of the spatial subregion in the image data set may include a segmentation of the contrast agent and/or of the medical object, in particular, of the distal section of the medical object, and/or of an anatomical object, for example, of a tissue and/or of an organ and/or an anatomical landmark, in the object under examination, wherein the at least one spatial point and/or region marks the change and/or the anatomical object. The spatial subregion in the image data set may advantageously be identified, such that the spatial subregion fully maps a spatial amplitude of the change, for example, a movement amplitude, and/or the anatomical object. In particular, the spatial subregion may include the at least one spatial point and/or region that was specified by the medical operative by the input in respect of the graphical representation of the image data set.

When specifying one or more points in time, in particular, within the initial period, and/or periods in the graphical representation of the image data set the temporal subregion in the image data set may advantageously be automatically identified, in particular, completed. For example, by the medical operative making an input the start and/or the end of the mapped change in the region of interest may be specified. Alternatively, or additionally, by the medical operative making an input a time period during the mapped change in the region of interest may be specified, wherein the start and/or the end of the change may be automatically identified. Since the spatiotemporal subregion in the image data set is delimited in time by the earliest start and/or the latest end of the change mapped at the locations within the region of interest, the spatial subregion in the image data set may advantageously be identified, such that it maps at least the location, in particular the spatial position, within the region of interest at which the change starts the earliest and/or ends the latest. As a result, it may advantageously be provided that the change in the region of interest of the object under examination is spatially and temporally fully mapped by the subregion of the image data set.

In accordance with a third variant of the proposed form of embodiment, the subregion of the image data set that maps the region of interest may be identified fully automatically. For the automatic identification of the spatial subregion in the image data set, for example, a mapping of the contrast agent and/or of the medical object, in particular, of the distal section of the medical object, and/or of the anatomical object in the image data set may be identified, in particular segmented. In this case, the spatial subregion in the image data set may be identified, such that it maps the contrast agent and/or the medical object, in particular the distal section of the medical object, and/or the anatomical object at least partially, in particular fully. Furthermore, for the automatic identification of the temporal subregion in the image data set, a mapped wash-in of the contrast agent and/or a mapped change in positioning of the medical object, in particular of the distal section of the medical object, and/or a mapped change in positioning of the anatomical object may be identified. In this case, the temporal subregion in the image data set may advantageously be identified, such that it is delimited in time by the earliest start and/or the latest end of the change mapped at the locations within the region of interest.

The automatic identification, in particular completion, of the spatial and/or temporal subregion in the image data set may advantageously be effected by applying a trained function, in particular an artificial intelligence, to the image data set as input data. The trained function may advantageously provide the spatial and/or the temporal subregion, in particular the spatiotemporal subregion, as output data.

The proposed form of embodiment may advantageously enable an application-oriented and/or intuitive identification of the subregion in the image data set that maps the region of interest.

In a further embodiment, the identification of the subregion in the image data set may include an identification of a mapping of an anatomical object and/or of a thrombus and/or of a vascular malformation and/or of a predefined section of a medical object arranged in the object under examination in the image data set and/or in a planning data set. In this case, the planning data set may be registered with the image data set and have a further mapping of the object under examination.

The identification of the mapping of the anatomical object and/or of the thrombus and/or of the vascular malformation and/or of the predefined section of the medical object arranged in the object under examination in the image data set and/or in the planning data set may for example be effected using geometric and/or anatomical features of the object to be identified, the geometric and/or anatomical features being mapped in the image data set and/or in the planning data set. The geometric features of the anatomical object and/or of the thrombus and/or of the vascular malformation and/or of the predefined section of the medical object arranged in the object under examination may include a contour and/or a contrast and/or a contrast distribution and/or a marker structure. Moreover, the anatomical features of the anatomical object and/or of the thrombus and/or of the vascular malformation may include a tissue border and/or anatomical landmarks and/or high-contrast objects. The identification of the mapping of the anatomical object and/or of the thrombus and/or of the vascular malformation and/or of the predefined section of the medical object arranged in the object under examination may include an identification, in particular segmentation, of the picture elements of the image data set, the picture elements mapping the anatomical object and/or the thrombus and/or the vascular malformation and/or the predefined section of the medical object arranged in the object under examination. In this case, the identification of the mapping of the anatomical object and/or of the thrombus and/or of the vascular malformation and/or of the predefined section of the medical object may be effected manually, semi-automatically, or fully automatically, in particular analogously to the identification of the subregion. In particular the mapping of the anatomical object and/or of the thrombus and/or of the vascular malformation and/or of the predefined section of the medical object may be identified by applying the trained function, in particular the artificial intelligence, to the image data set as input data. In this case, the trained function may provide the identified, in particular segmented, picture elements of the image data set to the spatial and/or the temporal subregion, in particular the spatiotemporal subregion, as the output data.

The anatomical object may include an organ, (e.g., a hollow organ and/or a brain and/or a liver and/or a heart and/or a lung), and/or a tissue and/or a tissue border. Furthermore, the thrombus may be a blood clot in the hollow organ which prevents a flow of blood and/or the movement of the contrast agent in the hollow organ by at least partial, in particular full, occlusion of the hollow organ. The vascular malformation may be embodied as an arteriovenous and/or venous and/or capillary vascular malformation, in particular an aneurysm and/or a nidus. The predefined section of the medical object may be the distal section, in particular a tip and/or an end region, of the medical object. Furthermore, the predefined section of the medical object may advantageously have the marker structure, the marker structure being mapped as a geometric feature in the image data set.

The planning data set may map the object under examination, in particular the anatomical object and/or the thrombus and/or the vascular malformation and/or the predefined section of the medical object, on a two-dimensionally and/or three-dimensionally spatially-resolved basis. Moreover, the planning data set may map the object under examination on a time-resolved basis, for example, prior to and/or during and/or after in time the acquisition of the image data set. In this case, the planning data set may have multiple further picture elements, in particular pixels and/or voxels, which map the object under examination. The planning data set may, by the same or a different medical imaging device, be acquired in the same way as the image data set.

Furthermore, prior to the start of the method, in particular after the acquisition of the planning data set and prior to the acquisition of the image data set, a thrombectomy, in particular a mechanical thrombectomy, of the thrombus in the hollow organ may have taken place. As a result, the image data set may advantageously map a recanalization of the hollow organ on a spatially and temporally resolved basis.

The proposed form of embodiment may enable an improved identification of the subregion in the image data set.

In a further embodiment, the region of interest may have a hollow organ. Moreover, the change may include a movement of the contrast agent in the hollow organ. In this case, the identification of the subregion may include establishing a spatial starting point in the hollow organ using the mapping of the object under examination and/or the further mapping of the object under examination. Furthermore, a spatial extent of the mapping of the region of interest in the image data set may be determined using the contrast agent in the hollow organ mapped downstream in respect of the starting point.

The movement of the contrast agent in the hollow organ may include a propagation movement and/or a flow movement of the contrast agent, in particular of a contrast agent bolus, in particular along a direction of longitudinal extent of the hollow organ. The spatial starting point may advantageously be established manually, semi-automatically, or fully automatically using the mapping of the object under examination, in particular, in the image data set and/or a graphical representation of the image data set, and/or using the further mapping of the object under examination, in particular in the planning data set and/or a graphical representation of the planning data set. For example, the starting point may be established by comparing the image data set with the planning data set. In this case, the starting point may specify a spatial position within the hollow organ, for example, on a center line of the hollow organ. Moreover, the earliest start of the change, in particular of the movement of the contrast agent, in the region of interest may be identified as the bolus arrival time at the spatial starting point. The spatial starting point may be established as a function of a mapped positioning of the medical object, in particular of the distal section of the medical object, and/or of an anatomical structure. The contrast agent may advantageously have a movement along a direction of flow in the hollow organ, in particular along the direction of longitudinal extent of the hollow organ. In this case, the downstream direction may run substantially parallel to the direction of flow of the contrast agent in the hollow organ. Furthermore, the downstream direction may run distally in respect of the starting point in the hollow organ. For this, linked regions and/or sections of the hollow organ that have a gradual filling behavior of the contrast agent may for example be identified using the image data set.

The image data set may map the object under examination, in particular, the region of interest, with an initial spatial resolution. In this case, the initial spatial resolution may specify an extent of the picture elements of the image data set. Furthermore, the initial spatial resolution may specify a maximum degree of detail for identifiability of the contrast agent in the image data set. Thanks to the arrangement of the contrast agent in the hollow organ a spatial extent of the contrast agent may be delimited by a diameter of the hollow organ. When the hollow organ is embodied as an artery and/or vein a reduction in the diameter of the hollow organ may take place in the downstream direction, in particular in the direction of blood flow. If the hollow organ has a diameter less than the initial spatial resolution of the image data set, the contrast agent may no longer be reliably identified in the image data set. The spatial extent of the mapping of the region of interest, in particular the spatial subregion, may advantageously be identified in the image data set, such that the contrast agent is fully mapped downstream in respect of the starting point in connection with the identifiability of the contrast agent.

Because the spatial extent of the mapping of the region of interest in the image data set is determined using the contrast agent in the hollow organ mapped downstream in respect of the starting point, a perfusion, in particular a reperfusion, of the hollow organ may advantageously be mapped in the result data set. In particular, the proposed form of embodiment may enable an evaluation of a recanalization of the hollow organ, in particular in the downstream direction in respect of the starting point. Prior to the start of the method a thrombectomy, in particular a mechanical thrombectomy, may have taken place in the hollow organ. In this case, a spatial position of a thrombus mapped in the planning data set may be specified as the starting point. Moreover, the subregion may be identified, such that the subregion maps the recanalized section of the hollow organ.

In a further embodiment, the region of interest may have a hollow organ. In this case, the hollow organ may have multiple different sections along its direction of longitudinal extent. Moreover, the change may include a movement of the contrast agent in the hollow organ. In this case, the different sections of the hollow organ in the result data set may in each case be assigned a bolus arrival time as the point in time of the start of the change in the respective section using the image data set.

The different sections along the direction of longitudinal extent of the hollow organ may be established using geometric and/or anatomical features. In this case, the different sections along the direction of longitudinal extent of the hollow organ may have at least partially, in particular fully, identical or different lengths. In particular, the different sections may each correspond to one or more picture elements of the image data set. Each of the different sections along the direction of longitudinal extent of the hollow organ may advantageously be assigned a bolus arrival time as the point in time of the start of the change, in particular the point in time of the wash-in of the contrast agent, in the respective section using the image data set, in particular the time intensity curves of the picture elements of the image data set. The assignment of the bolus arrival time to the different sections along the direction of longitudinal extent of the hollow organ may include an assignment of numerical values. The result data set may advantageously have a data structure that maps the region of interest with the different sections along the direction of longitudinal extent of the hollow organ on a spatially and temporally resolved basis, wherein the different sections are assigned the respective bolus arrival time. The provision of the result data set may advantageously include a display of a graphical representation of the bolus arrival time of the different sections along the direction of longitudinal extent of the hollow organ, for example, by a color-coded graphical representation of the hollow organ. As a result, a medical operative may advantageously be supported during the acquisition of hemodynamic parameters, for example, a blood flow speed, in the hollow organ.

Alternatively, or additionally, at least one spatial end point, in particular in each case a spatial end point for each branch of the hollow organ, may be identified using the image data set, the at least one spatial end point having no spatial point with gradual contrast agent filling along the direction of longitudinal extent of the hollow organ. The provision of the result data set may advantageously include marking the at least one end point in the mapping of the region of interest. As a result, the medical operative may advantageously be supported during the acquisition of distal emboli.

By assigning the bolus arrival time to the different sections along the direction of longitudinal extent of the hollow organ, the result data set may contain hemodynamic information in addition to the spatiotemporally resolved mapping of the hollow organ.

In a further embodiment, the acquisition of the image data set may include an acquisition of first and second image data. In this case, the first image data may map the object under examination in a first temporal phase prior to the start of the change. Furthermore, the second image data may map the object under examination in a second temporal phase after the first temporal phase. In this case, the change in the object under examination may have taken place after the first temporal phase and during the second temporal phase. Furthermore, the image data set may be provided on the basis of a comparison of the first and second image data.

The first and the second image data may be acquired by the same or different medical imaging devices. The first and the second image data are advantageously registered at least spatially with one another. The first and the second image data may advantageously in each case include a two-dimensional and/or three-dimensional mapping of the object under examination. Moreover, the first and/or the second image data may map the object under examination on a time-resolved basis. The first and/or the second image data may in each case be reconstructed from multiple individual images, each of which has a mapping of at least one part of the object under examination. The first image data may map the object under examination in the first temporal phase, in particular a mask phase, prior to the start of the change. The first image data may advantageously map the initial state of the object under examination. Furthermore, the second image data may map the object under examination in the second temporal phase, in particular a filling phase, after the first temporal phase. The first and the second temporal phase may in this case each include at least one, in particular multiple, acquisition time points. In this case, the change in the object under examination may have taken place after the first temporal phase and during the second temporal phase. In particular, the movement of the medical object, in particular of the distal section of the medical object, and/or the movement of the contrast agent may have taken place after the first temporal phase and during the second temporal phase. The image data set may be provided on the basis of the comparison of the first and second image data. In particular, the image data set may include a difference image that was provided by subtraction of the first and second image data. As a result, the image data set may advantageously map the change in the object under examination, in particular in respect of the first temporal phase.

Moreover, an improved identification of the subregion in the image data set, in particular for the acquisition of the change in the region of interest, may as a result be enabled.

In a further embodiment, the image data set having an initial temporal and spatial resolution may be reconstructed. In this case, the result data set having a higher temporal and/or spatial resolution in respect of the initial temporal and/or spatial resolution may be reconstructed.

The image data set may be reconstructed from multiple individual images and/or raw data, in particular frequency data, having the initial temporal and spatial resolution. In this case, the initial temporal and spatial resolution may be specified, in particular delimited, by a reconstruction parameter, in particular a further input by the medical operative, and/or an acquisition parameter of the individual images and/or of the raw data. The initial spatial resolution may be isotropic or anisotropic. Furthermore, the acquisition parameter may be an intrinsic and/or extrinsic parameter of the medical imaging device, for example, a resolution of detector pixels, a distance between source and object under examination and/or a distance between source and detector. Moreover the initial temporal resolution may be delimited by a frame rate as an acquisition parameter during the acquisition of the image data set.

The identification of the spatiotemporal subregion in the image data set may include an identification of the individual images and/or of the raw data, which map the change in the region of interest. The result data set may advantageously be reconstructed from the identified individual images and/or raw data, which map the change in the region of interest, having the higher temporal and/or spatial resolution in respect of the initial temporal and/or spatial resolution. In this case, the temporal and/or spatial resolution of the result data set may be specified, in particular delimited, by a further reconstruction parameter and/or an acquisition parameter of the individual images and/or of the raw data, the individual images and/or raw data being used for the reconstruction of the result data set. The spatial resolution of the result data set may be isotropic or anisotropic. In particular, the result data set may have a higher temporal resolution in respect of the initial temporal resolution. Alternatively, or additionally, the result data set may have a higher spatial resolution in respect of the initial spatial resolution.

As a result, an improved mapping of the change in the region of interest in the result data set is enabled. Small anatomical objects, (e.g., vessels and/or vessel sections with a small diameter), frequently have a potentially large influence on treatment options and/or an outcome of treatment, in particular a treatment risk. Thanks to the improved temporal and/or spatial resolution of the result data set, the medical operative may advantageously be supported when planning the treatment strategy, for example, for an embolization, and/or the treatment plan, in particular the endovascular treatment plan.

In a further embodiment, the acquisition of the image data set may include an acquisition of multiple projection mappings of the object under examination with at least partially different mapping geometry. In this case, the image data set may be reconstructed from the multiple projection mappings. Moreover, the result data set may be reconstructed from the projection mappings that map the region of interest.

The acquisition of the image data set may advantageously include an acquisition of the multiple projection mappings, in particular multiple X-ray projection mappings, of the object under examination with at least partially, in particular fully, different mapping geometry. The mapping geometry may describe a projection direction, in particular an angulation, for the acquisition of the multiple projection mappings of the object under examination. The multiple projection mappings may advantageously map the object under examination from at least partially, in particular fully, different projection directions. In particular, the multiple projection mappings may be acquired during at least one rotational pass, in particular multiple rotational passes, around the object under examination. The reconstruction of the image data set from the multiple projection mappings may include a filtered back-projection and/or an inverse radon transformation and/or an iterative reconstruction, in particular a statistical and/or model-based iterative reconstruction. Furthermore, the reconstruction of the result data set from the projection mappings that map the region of interest of the object under examination may include a filtered back-projection and/or an inverse radon transformation and/or an iterative reconstruction, in particular a statistical and/or model-based iterative reconstruction.

If the acquisition of the image data set includes an acquisition of first and second image data, the first image data may have at least one first projection mapping, (e.g., multiple first projection mappings), of the object under examination and/or the second image data may have multiple second projection mappings of the object under examination. In this case, the at least one first projection mapping may map the object under examination in the first temporal phase prior to the start of the change. Furthermore, the multiple second projection mappings may map the object under examination in the second temporal phase after the first temporal phase.

By mapping the object under examination from at least partially, in particular fully, different projection directions an improved reconstruction of the object under examination, in particular, of complex anatomical objects of the object under examination, may be enabled in the image data set and/or the result data set. Moreover, by reconstructing the result data set from the projection mappings that map the region of interest an especially computationally efficient reconstruction may be enabled.

In a further embodiment, the reconstruction of the result data set may be based on the image data set as a consistency condition.

Arranging multiple anatomical objects, (e.g., multiple hollow organs), and/or multiple sections of an anatomical object, (e.g., multiple vessel sections), along a projection direction for the acquisition of at least one of the multiple projection mappings, may result in the superimposed mapping of the multiple anatomical objects and/or the multiple sections of the anatomical object in the at least one projection mapping. The image data set is advantageously reconstructed from the multiple projection mappings, in particular all available projection mappings. In this case, the multiple projection mappings of the object under examination may be mapped from the at least partially, in particular fully, different projection directions, so that a superimposed mapping of multiple anatomical objects and/or multiple sections of an anatomical object may be resolved during the reconstruction of the image data set. Furthermore, the result data set is reconstructed from the projection mappings of the multiple projection mappings, the projection mappings mapping the region of interest. In this case, it may happen that only some of the multiple projection mappings are used for the reconstruction of the result data set. Furthermore, it may as a result happen that a superimposed mapping of multiple anatomical objects and/or of multiple sections of an anatomical object cannot be unambiguously resolved during the reconstruction of the result data set. The image data set, in particular the mapping of the multiple anatomical objects and/or of the multiple sections of the anatomical object in the image data set, may advantageously be used as a consistency condition for the reconstruction of the result data set. As a result, image values of picture elements of the projection mappings that are used for the reconstruction of the result data set and that map multiple anatomical objects and/or multiple sections of an anatomical object on a superimposed basis, may, on the basis of the image data set as a consistency condition, be unambiguously resolved, in particular identified.

A second aspect of the disclosure relates to a provision unit, which is configured for the execution of an advantageous form of embodiment of the proposed method for providing a result data set.

The advantages of the proposed provision unit substantially correspond to the advantages of the proposed method for providing a result data set. Features, advantages, or alternative forms of embodiment mentioned here may likewise also be transferred to the other objects claimed and vice versa.

The provision unit may advantageously include a computing unit (e.g., having a processor and memory), a storage unit, and/or an interface. In this case, the provision unit, in particular the components of the provision unit, may be configured to execute the individual acts of the proposed method for providing a result data set. In particular, the interface may be configured to control the medical imaging device for the acquisition of the image data set and/or to receive the image data set from the medical imaging device. Furthermore, the computing unit and/or the storage unit may be configured for the identification of the spatiotemporal subregion in the image data set. Furthermore, the interface may be configured for the provision of the result data set on the basis of the subregion of the image data set.

A third aspect of the disclosure relates to a medical imaging device having a proposed provision unit. In this case, the medical imaging device is designed to acquire the image data set.

The medical imaging device may be configured as a magnetic resonance tomography system (MRT) and/or a computed tomography system (CT) and/or a medical X-ray device and/or a positron emission tomography system (PET) and/or an ultrasound device. In this case, the medical imaging device may be configured for the acquisition of the image data set of the object under examination.

The advantages of the proposed medical imaging device substantially correspond to the advantages of the proposed method for providing a result data set and/or the proposed provision unit. Features, advantages, or alternative forms of embodiment mentioned here may likewise also be transferred to the other objects claimed and vice versa.

A fourth aspect of the disclosure relates to a computer program product having a computer program that may be loaded directly into a memory of a provision unit, having program sections in order to execute all acts of the method for providing a result data set when the program sections are executed by the provision unit.

The disclosure may further relate to a computer-readable storage medium, on which program sections that may be read and executed by a provision unit are stored, in order to execute all acts of the method for providing a result data set when the program sections are executed by the provision unit.

A largely software-based implementation has the advantage that even previously used provision units may also easily be retrofitted by a software update in order to work in the manner in accordance with the disclosure. A computer program product such as this may if appropriate include, besides the computer program, additional components such as documentation and/or additional components, as well as hardware components, such as hardware keys (e.g., dongles, etc.) for the use of the software.

BRIEF DESCRIPTION OF THE DRAWINGS

Exemplary embodiments of the disclosure are represented in the drawings and are described in greater detail below. The same reference characters are used for the same features in different figures, in which.

DETAILED DESCRIPTION

Figure 1:
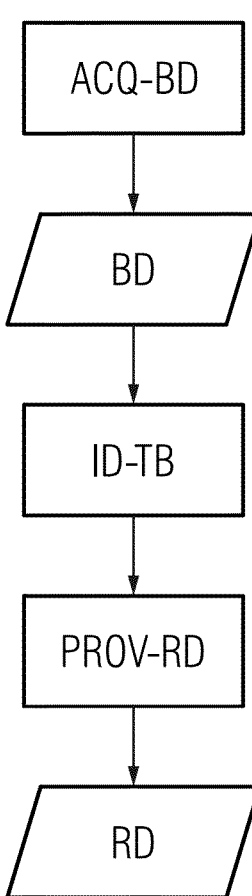
FIGS. 1 to 3 depict schematic representations of different examples of methods for providing a result data set.

FIG. 1 schematically shows an advantageous form of embodiment of a proposed method for providing a result data set PROV-RD. In this case, a medical image data set BD of an object under examination may be acquired ACQ-BD. The image data set BD may advantageously map a change in the object under examination. In this case, the change may start and/or end at different locations within the object under examination at at least partially different points in time. In a further act, a spatiotemporal subregion in the image data set BD may be identified ID-TB. In this case, the subregion may be delimited spatially by the mapping of the region of interest and temporally by the earliest start and/or the latest end of the change mapped at the locations within the region of interest. After this, the result data set RD based on the subregion of the image data set BD may be provided PROV-RD. In this case, the result data set RD may map the region of interest on a time-resolved basis.

The change may advantageously include a movement of a contrast agent and/or of a medical object at least in the region of interest of the object under examination. Moreover, the subregion of the image data set BD mapping the region of interest may be identified manually, semi-automatically or fully automatically ID-TB.

The region of interest may have a hollow organ, in particular an artery and/or vein. In this case, the change may include a movement of the contrast agent in the hollow organ. Furthermore, the identification of the subregion ID- TB may include an establishment of a spatial starting point in the hollow organ using the mapping of the hollow organ and/or the further mapping of the hollow organ. In this case, a spatial extent of the mapping of the region of interest may be determined in the image data set BD using the contrast agent in the hollow organ mapped downstream in respect of the starting point.

Furthermore, the hollow organ may have multiple different sections along its direction of longitudinal extent. In this case, the different sections of the hollow organ in the result data set RD may each be assigned a bolus arrival time as the point in time of the start of the change, in particular a wash-in of the contrast agent, in the respective section using the image data set BD.

Figure 2:
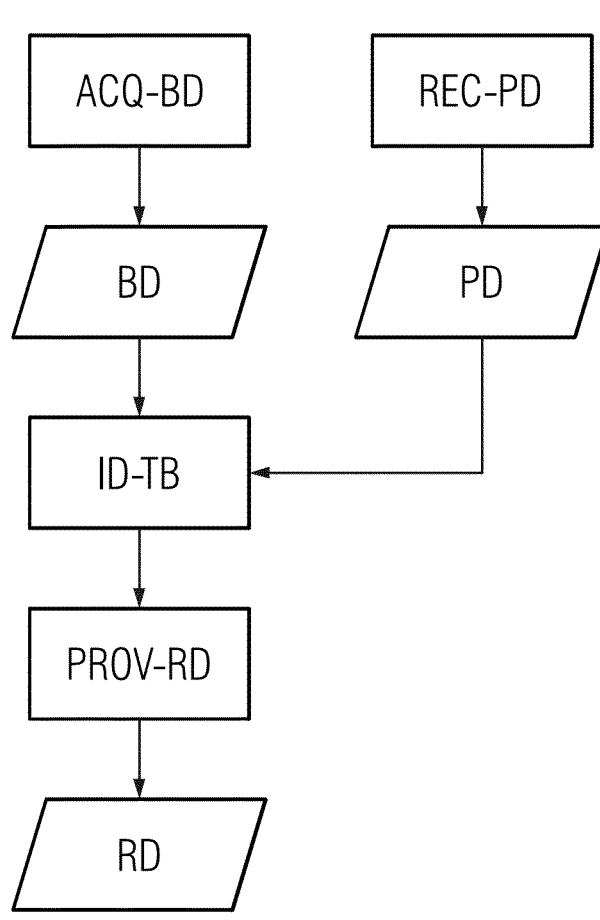

FIG. 2 shows a schematic representation of a further advantageous form of embodiment of a method for providing a result data set PROV-RD. In this case, the identification of the subregion ID-TB in the image data set BD may include an identification of a mapping of an anatomical object and/or of a thrombus and/or of a vascular malformation and/or of a predefined section of a medical object arranged in the object under examination in the image data set BD and/or in a planning data set PD. The planning data set PD may be acquired by the same or a different medical imaging device as was used for the image data set BD. Furthermore, the planning data set PD may be received as part of the proposed method REC-PD. The planning data set PD may advantageously be registered with the image data set BD. Furthermore, the planning data set PD may have a further mapping of the object under examination.

Figure 3:
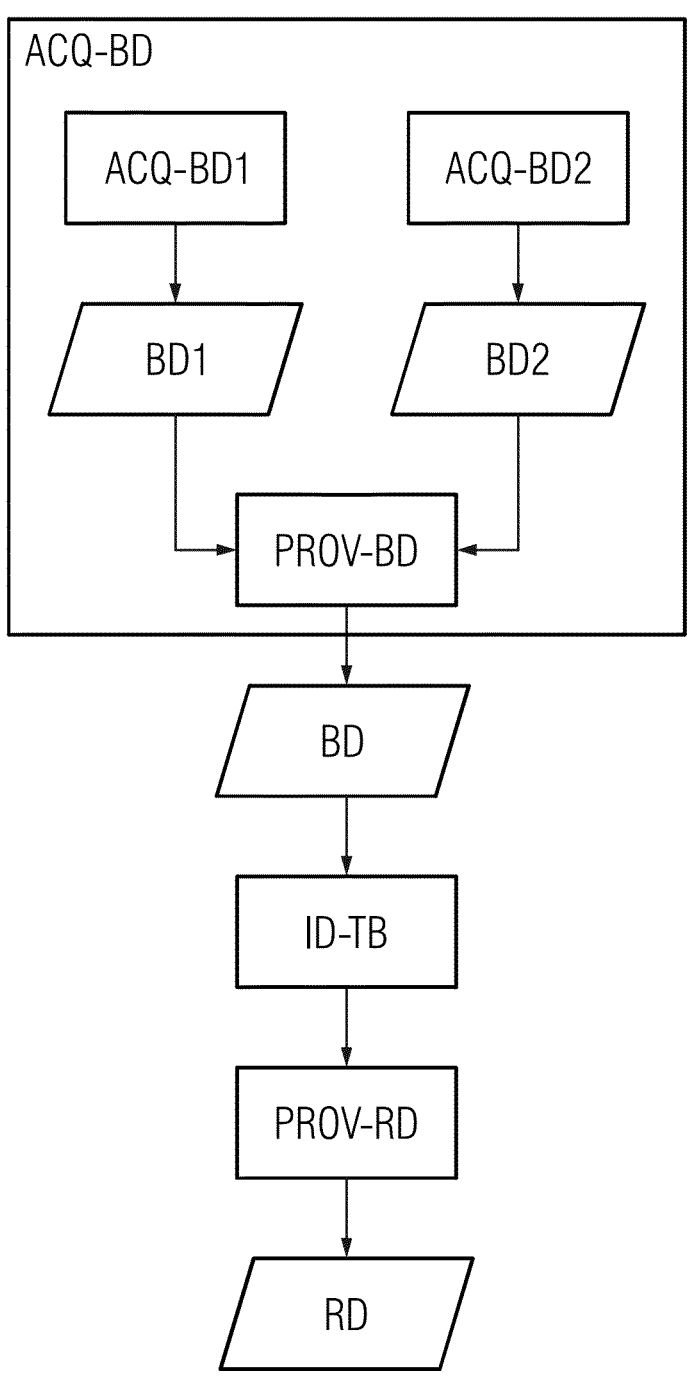

FIG. 3 schematically shows a further advantageous form of embodiment of a proposed method for providing a result data set PROV-RD. In this case, the acquisition of the image data set ACQ-BD may include an acquisition of first and second image data ACQ-BD1 and ACQ-BD2. The first image data BD1 may map the object under examination in a first temporal phase prior to the start of the change. Furthermore, the second image data BD2 may map the object under examination 31 in a second temporal phase after the first temporal phase. In this case the change in the object under examination may have taken place after the first temporal phase and during the second temporal phase. Moreover the image data set BD may be provided on the basis of a comparison of the first BD1 and second image data BD2.

The acquisition of the image data set ACQ-BD may advantageously include an acquisition of multiple projection mappings with at least partially different mapping geometry of the object under examination. For example, the first image data BD1 may have at least one first projection mapping, in particular multiple first projection mappings, and/or the second image data BD2 may have multiple second projection mappings of the object under examination 31. In this case, the image data set BD, having an initial temporal and spatial resolution, may be reconstructed from the at least one first and the multiple second projection mappings. Furthermore, the result data set RD may be reconstructed from the projection mappings, in particular the at least one first projection mapping and at least some of the multiple second projection mappings that map the region of interest. The result data set RD having a higher temporal and/or spatial resolution in respect of the initial temporal and/or spatial resolution may advantageously be reconstructed. In this case the reconstruction of the result data set RD may be based on the image data set BD as a consistency condition.

Figure 4:
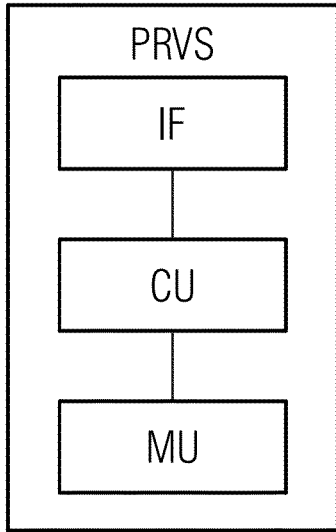
FIG. 4 depicts a schematic representation of an example of a provision unit.

FIG. 4 shows a schematic representation of an advantageous form of embodiment of a proposed provision unit PRVS. The provision unit PRVS may advantageously include a computing unit CU, a storage unit MU and/or an interface IF. In this case, the provision unit PRVS, in particular the components of the provision unit PRVS, may be designed to execute the individual acts of the proposed method for providing a result data set PROV-RD. In particular, the interface IF may be designed to control the medical imaging device for the acquisition of the image data set ACQ-BD and/or to receive the image data set BD from the medical imaging device. Furthermore, the computing unit CU and/or the storage unit MU may be designed for the identification of the spatiotemporal subregion ID-TB in the image data set BD. Furthermore, the interface IF may be designed for the provision of the result data set PROV-RD on the basis of the subregion of the image data set BD.

Figure 5:
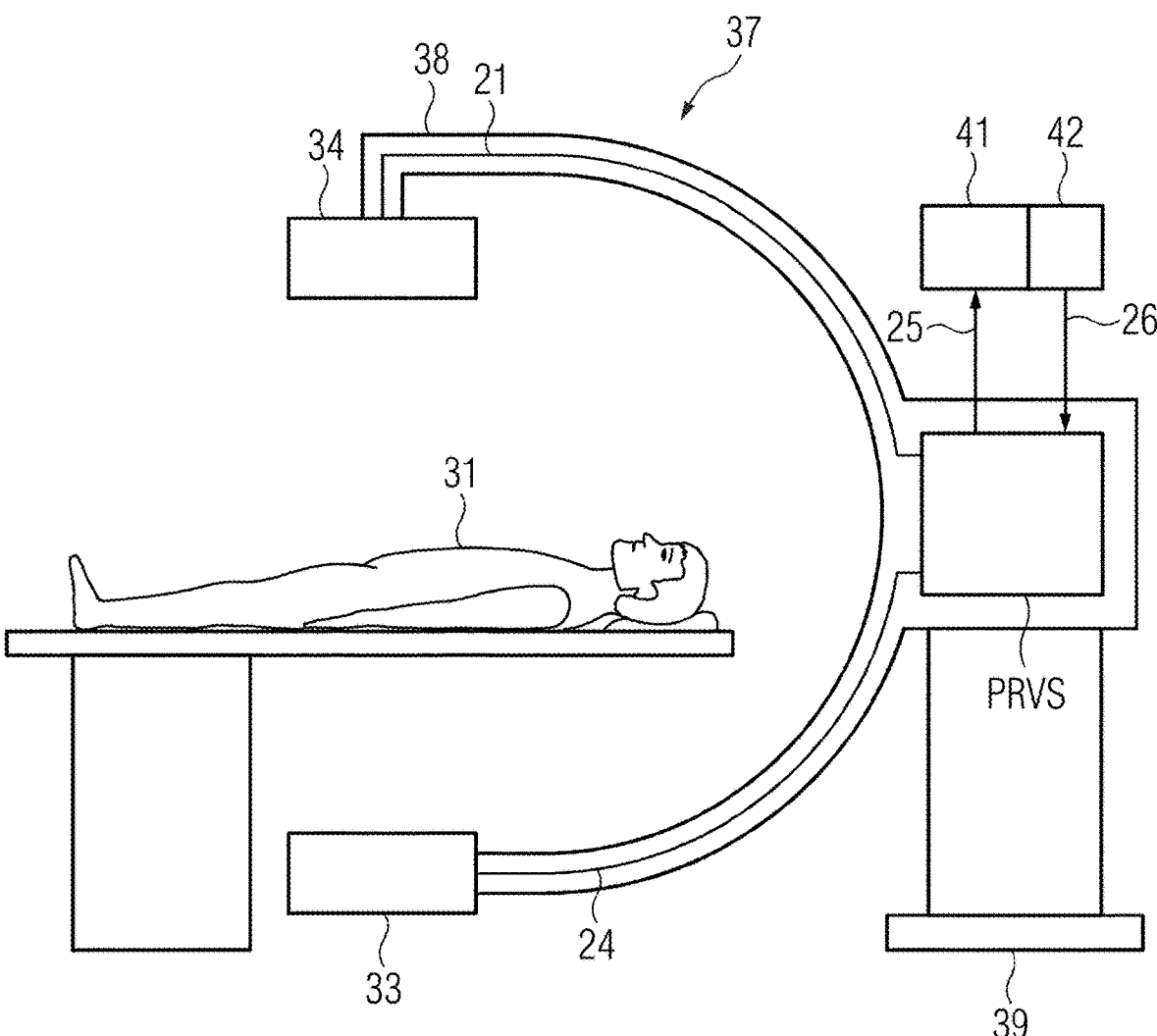
FIG. 5 depicts a schematic representation of an example of a medical imaging device.

FIG. 5 shows, by way of example for a proposed medical imaging device, a schematic representation of a medical C-arm X-ray device 37. Here, the medical C-arm X-ray device 37 advantageously includes a detector 34, in particular an X-ray detector, and an X-ray source 33. Furthermore, the medical C-arm X-ray device 37 may be designed for the acquisition of the image data set ACQ-BD. For the acquisition of the image data set ACQ-BD an arm 38 of the C-arm X-ray device 37 may be movably mounted about one or more axes. Furthermore, the medical C-arm X-ray device 37 may include a movement unit 39 that enables a movement of the C-arm X-ray device 37 in space. Moreover, the provision unit PRVS for the acquisition of the image data set ACQ-BD may send a corresponding signal 24 to the X-ray source 33. Thereupon, the X-ray source 33 may emit an X-ray beam. When the X-ray beam, after an interaction with the object under examination 31, hits a surface of the detector 34, the detector 34 may send a signal 21 to the provision unit PRVS. The provision unit PRVS may receive, using the signal 21, the image data set BD of the object under examination 31.

Furthermore, the medical imaging device 37 may have an input unit 42, (e.g., a keyboard), and a display unit 41, (e.g., a monitor and/or display). The input unit 42 may be integrated into the display unit 41, for example, in the case of a capacitive and/or resistive input display. The display unit 41 may advantageously be configured to display a graphical representation of the image data set and/or of the result data set. For this, the provision unit PRVS may send a signal 25 to the display unit 41. The input unit 42 may be configured for the acquisition of an input by a medical operative. In this case, control of the medical C-arm X-ray device 37 may be enabled on the basis of the acquired input of the medical operative. For this, the input unit 42 may send a signal 26 to the provision unit PRVS.

The schematic representations contained in the described figures do not map the scale or proportions.

In conclusion, it is once again noted that the methods and apparatuses described in detail above relate solely to exemplary embodiments that may be modified by the person skilled in the art in a variety of ways, without departing from the scope of the disclosure. Further, the use of the indefinite article "a" or "an" does not rule out that the features in question may also be present multiple times. Likewise the terms "unit" and "element" do not rule out that the components in question include multiple interacting subcomponents that if appropriate may also be distributed spatially.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the disclosure has been illustrated and described in detail with the help of the embodiments, the disclosure is not limited to the disclosed examples. Other variations may be deduced by those skilled in the art without leaving the scope of protection of the claimed disclosure.

The invention claimed is:

1. A method for providing a result data set, the method comprising:

acquiring a medical image data set of an object under examination, wherein the medical image data set maps a change in the object under examination on a time-resolved basis, and wherein the change starts and/or ends at different locations and at different points in time within the object under examination;

identifying a spatiotemporal subregion in the medical image data set, wherein the spatiotemporal subregion maps the change in a region of interest of the object under examination, wherein the spatiotemporal subregion is delimited spatially by the mapping of the region of interest and temporally by an earliest start and a latest end of the change mapped at the different locations within the region of interest, and wherein the earliest start and the latest end of the change are determined by comparing points in time of the start and/or the end of the change at the different locations within the region of interest; and providing the result data set based on the subregion of the medical image data set, wherein the result data set maps the region of interest on a time-resolved basis.

2. The method of claim 1, wherein the change in the region of interest comprises a movement of a contrast agent and/or a movement of a medical object at least in the region of interest.

3. The method of claim 2, wherein the subregion of the medical image data set mapping the region of interest is identified manually, semi-automatically, or fully automatically.

4. The method of claim 1, wherein the subregion of the medical image data set mapping the region of interest is identified manually, semi-automatically, or fully automatically.

5. The method of claim 4, wherein the identifying of the subregion in the medical image data set comprises identifying a mapping of one or more of an anatomical object, a thrombus, a vascular malformation, or a predefined section of a medical object arranged in the object under examination in the medical image data set and/or in a planning data set, and wherein the planning data set is registered with the medical image data set and has a further mapping of the object under examination.

6. The method of claim 5, wherein the region of interest has a hollow organ, wherein the change in the region of interest comprises a movement of a contrast agent in the hollow organ, wherein the identifying of the spatiotemporal subregion comprises establishing a spatial starting point in the hollow organ using the mapping of the object under examination and/or the further mapping of the object under examination, and wherein a spatial extent of the mapping of the region of interest in the medical image data set is determined in the hollow organ using the contrast agent mapped downstream in respect of the starting point.

7. The method of claim 5, wherein the region of interest has a hollow organ, wherein the hollow organ has multiple different sections along a direction of longitudinal extent of the hollow organ, wherein the change in the region of interest comprises a movement of a contrast agent in the hollow organ, and wherein each section of the multiple different sections of the hollow organ in the result data set is assigned a bolus arrival time as a point in time of a start of the change in the respective section using the medical image data set.

8. The method of claim 5, wherein the acquiring of the medical image data set comprises acquiring first image data and second image data, wherein the first image data maps the object under examination in a first temporal phase prior to a start of the change, wherein the second image data maps the object under examination in a second temporal phase after the first temporal phase, wherein the change in the object under examination has taken place after the first temporal phase and during the second temporal phase, and wherein the medical image data set is provided based on a comparison of the first image data and the second image data.

9. The method of claim 5, wherein the medical image data set having an initial temporal resolution and an initial spatial resolution is reconstructed, and wherein the result data set having a higher temporal and/or spatial resolution with respect to the initial temporal resolution and/or the initial spatial resolution is reconstructed.

10. The method of claim 5, wherein the acquiring of the medical image data set comprises acquiring multiple projection mappings with different mapping geometry of the object under examination, wherein the medical image data set is reconstructed from the multiple projection mappings, and wherein the result data set is reconstructed from the multiple projection mappings that map the region of interest.

11. The method as claimed in claim 10, wherein the reconstruction of the result data set is based on the medical image data set as a consistency condition.

12. The method of claim 1, wherein the acquiring of the medical image data set comprises acquiring first image data and second image data, wherein the first image data maps the object under examination in a first temporal phase prior to the start of the change, wherein the second image data maps the object under examination in a second temporal phase after the first temporal phase, wherein the change in the object under examination has taken place after the first temporal phase and during the second temporal phase, and wherein the medical image data set is provided based on a comparison of the first image data and the second image data.

13. The method of claim 1, wherein the medical image data set having an initial temporal resolution and an initial spatial resolution is reconstructed, and wherein the result data set having a higher temporal and/or spatial resolution with respect to the initial temporal resolution and/or the initial spatial resolution is reconstructed.

14. The method of claim 1, wherein the acquiring of the medical image data set comprises acquiring multiple projection mappings with different mapping geometry of the object under examination, wherein the medical image data set is reconstructed from the multiple projection mappings, and wherein the result data set is reconstructed from the projection mappings that map the region of interest.

15. The method as claimed in claim 14, wherein the reconstruction of the result data set is based on the medical image data set as a consistency condition.

16. A provision unit comprising:

a computing unit having a processor and memory, wherein the processor and memory are configured to:

acquire a medical image data set of an object under examination, wherein the medical image data set maps a change in the object under examination on a time-resolved basis, and wherein the change starts and/or ends at different locations and different points in time within the object under examination; and identify a spatiotemporal subregion in the medical image data set, wherein the spatiotemporal subregion maps the change in a region of interest of the object under examination, wherein the spatiotemporal subregion is delimited spatially by the mapping of the region of interest and temporally by an earliest start and a latest end of the change mapped at the locations within the region of interest, and wherein the earliest start and the latest end of the change are determined by comparing points in time of the start and/or the end of the change at the different locations within the region of interest; and an interface configured to provide a result data set based on the subregion of the medical image data set, wherein the result data set maps the region of interest on a time-resolved basis.

17. A medical imaging device comprising:

a processor and a memory configured to:

acquire a medical image data set of an object under examination, wherein the medical image data set maps a change in the object under examination on a time-resolved basis, and wherein the change starts and/or ends at different locations and different points in time within the object under examination; and identify a spatiotemporal subregion in the medical image data set, wherein the spatiotemporal subregion maps the change in a region of interest of the object under examination, wherein the spatiotemporal subregion is delimited spatially by the mapping of the region of interest and temporally by an earliest start and a latest end of the change mapped at the locations within the region of interest, and wherein the earliest start and the latest end of the change are determined by comparing points in time of the start and/or the end of the change at the different locations within the region of interest; and provide a result data set based on the subregion of the medical image data set, wherein the result data set maps the region of interest on a time-resolved basis.

* * * * *